(12) United States Patent
Dicesare et al.

(10) Patent No.: US 7,105,004 B2
(45) Date of Patent: Sep. 12, 2006

(54) ONE-HAND LOCKING AND RELEASING HANDHELD MEDICAL INSTRUMENT

(75) Inventors: Paul Dicesare, Easton, CT (US); Jeffrey P. Radziunas, Wallingford, CT (US)

(73) Assignee: Start LLC, Norwalk, CT (US)

( * ) Notice: Subject to any disclaimer, the term of this patent is extended or adjusted under 35 U.S.C. 154(b) by 267 days.

(21) Appl. No.: 10/689,293

(22) Filed: Oct. 20, 2003

(65) Prior Publication Data
US 2004/0167569 A1    Aug. 26, 2004

Related U.S. Application Data

(60) Provisional application No. 60/419,582, filed on Oct. 21, 2002.

(51) Int. Cl.
  B65B 7/02   (2006.01)
  A61B 17/00  (2006.01)
  A61B 17/28  (2006.01)
  A61B 17/50  (2006.01)

(52) U.S. Cl. ................ 606/170; 81/313; 81/319; 81/320; 81/329; 81/331; 606/139; 606/142; 606/205

(58) Field of Classification Search ............. 81/319, 81/320, 329, 331
See application file for complete search history.

(56) References Cited

U.S. PATENT DOCUMENTS

| | | | |
|---|---|---|---|
| 4,674,504 A | 6/1987 | Klieman et al. ............. 128/325 |
| 5,067,958 A | 11/1991 | Sandhaus .................... 606/142 |
| 5,176,702 A * | 1/1993 | Bales et al. ................. 606/208 |
| 5,376,094 A | 12/1994 | Kline .......................... 606/113 |
| 5,456,684 A | 10/1995 | Schmidt ....................... 606/41 |
| 5,476,479 A * | 12/1995 | Green et al. ................. 606/205 |
| 5,607,436 A | 3/1997 | Pratt et al. ................... 606/143 |
| 5,609,601 A * | 3/1997 | Kolesa et al. ............... 606/170 |
| 5,611,813 A * | 3/1997 | Lichtman .................... 606/205 |
| 5,626,608 A | 5/1997 | Cuny et al. ................. 606/205 |
| 5,700,270 A * | 12/1997 | Peyser et al. ............... 606/142 |
| 5,938,667 A | 8/1999 | Peyser et al. ............... 606/142 |
| 6,066,146 A | 5/2000 | Carroll ....................... 606/148 |
| 6,117,158 A * | 9/2000 | Measamer et al. .......... 606/208 |
| 6,258,101 B1 | 7/2001 | Blake, III ................... 606/113 |
| 6,299,625 B1 * | 10/2001 | Bacher ....................... 606/170 |
| 6,383,195 B1 | 5/2002 | Richard ...................... 606/114 |

* cited by examiner

Primary Examiner—Michael J. Hayes
Assistant Examiner—M. Thomas Andersen
(74) Attorney, Agent, or Firm—Perman & Green, LLP

(57) ABSTRACT

Locking and releasing apparatus for operating a medical device includes a handle and a lever member coupled to the handle for grasping engagement by an operator. The lever member is moveable in opposite directions relative to the handle. A locking and release mechanism operably connects the lever member to a force transmitting member for operating the medical device at a location distant from the handle. The locking and release mechanism locks movement of the force transmitting member in one direction after movement of the lever member in a locking direction. The locking and release mechanism releases movement of the force transmitting member in the one direction after opposite movement of the lever member in a releasing direction. The lever member operates the locking and release mechanism for releasing the movement of the force transmitting member in the one direction substantially upon changing movement of the lever member from the locking to the releasing direction.

20 Claims, 14 Drawing Sheets

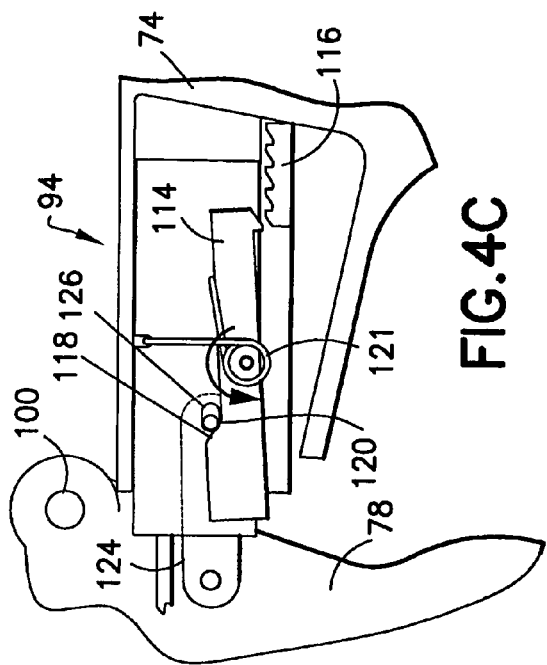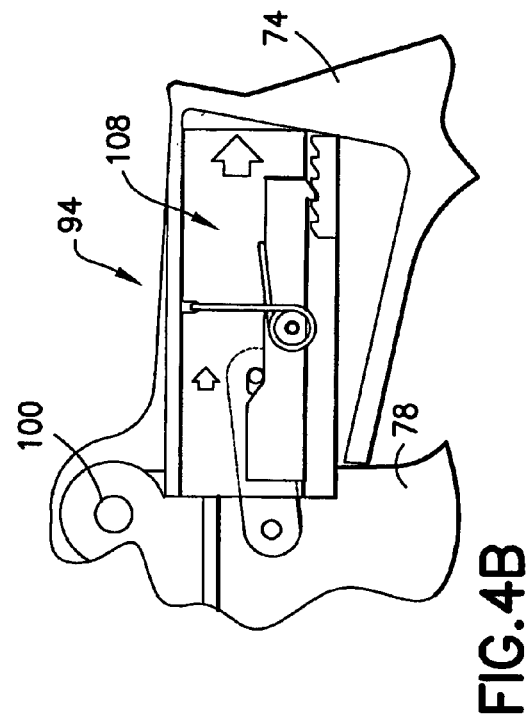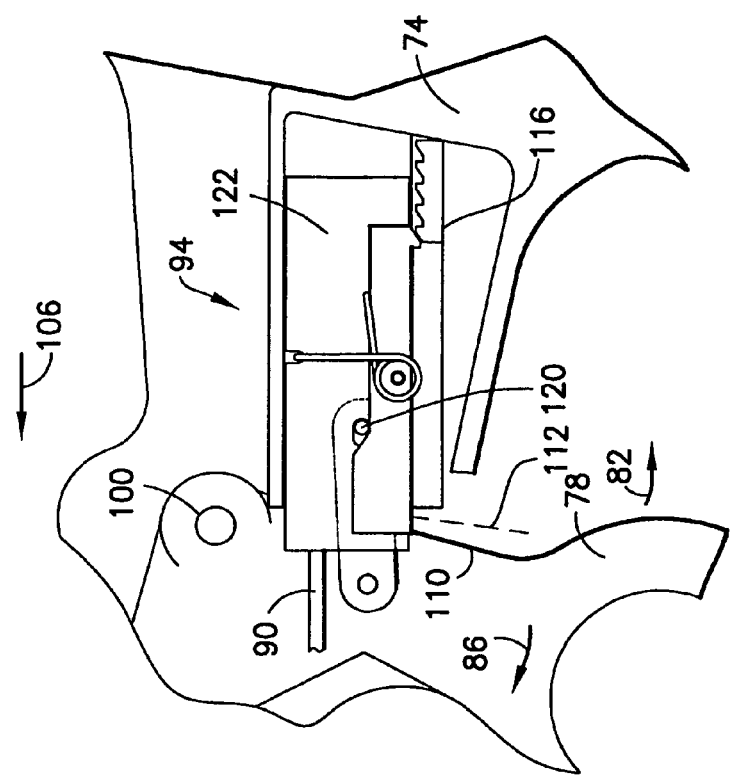

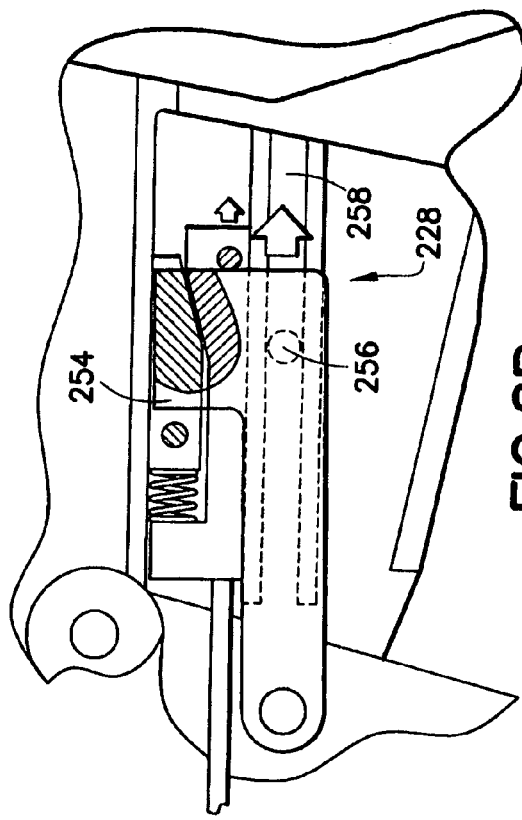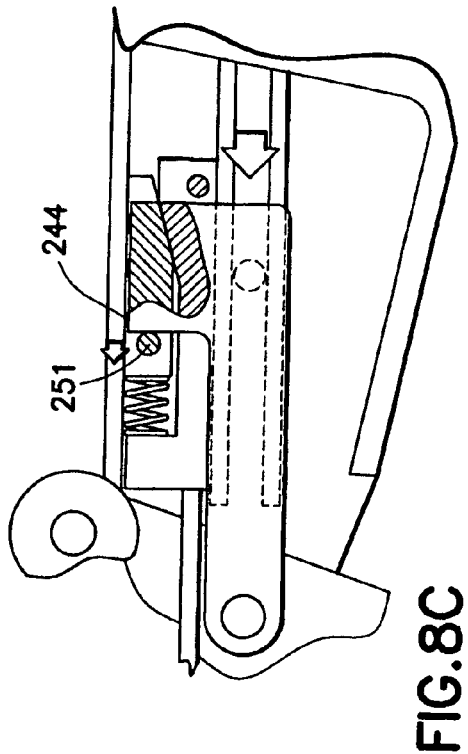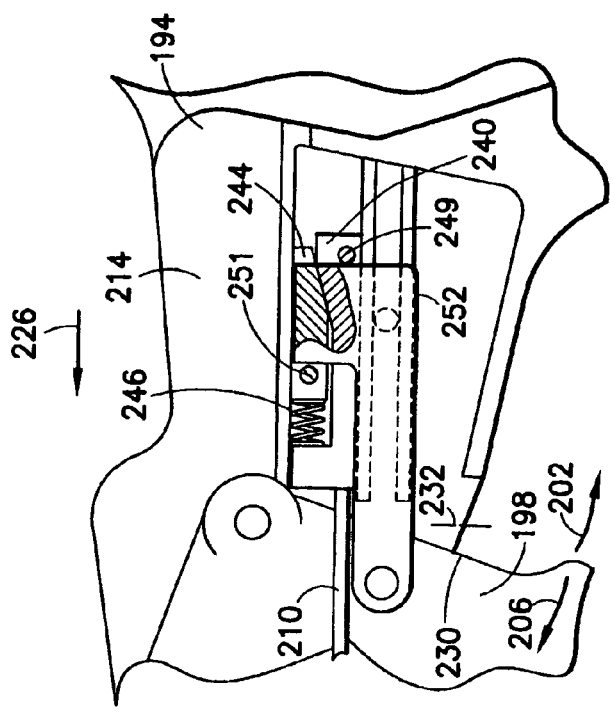

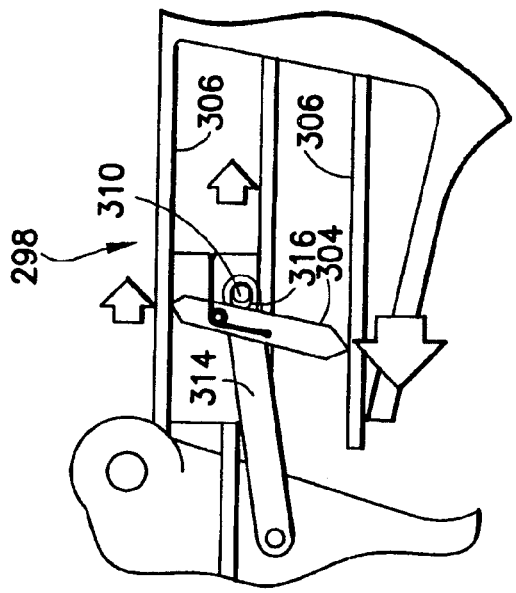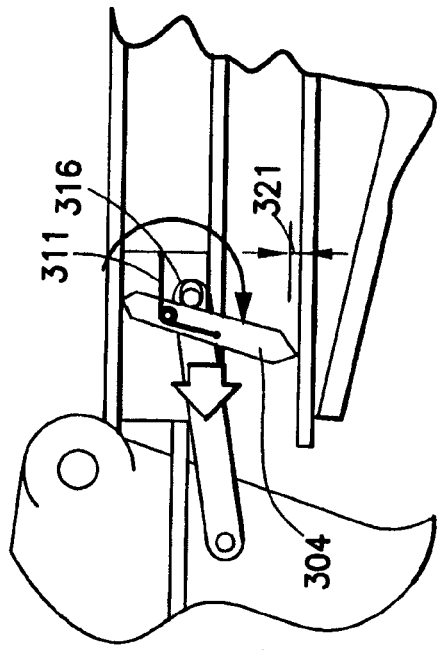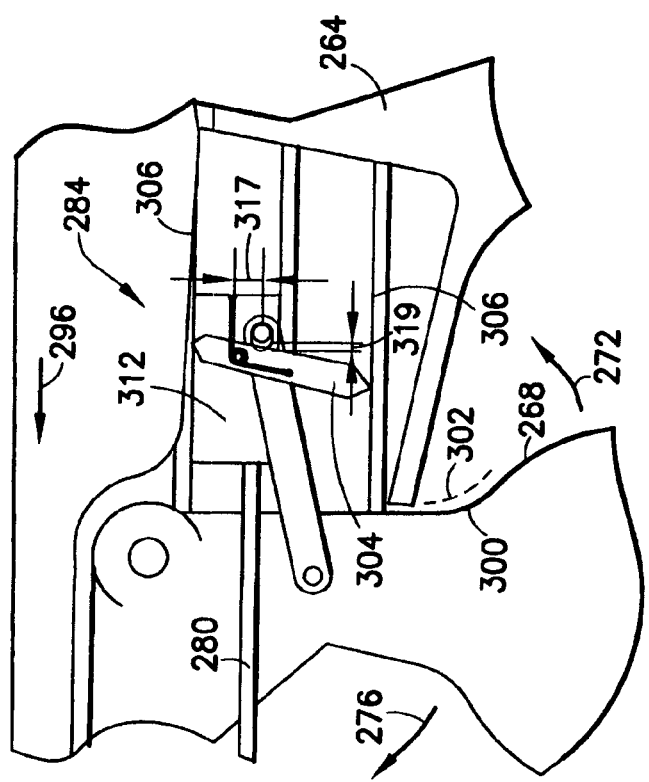
FIG.10B
FIG.10C
FIG.10A

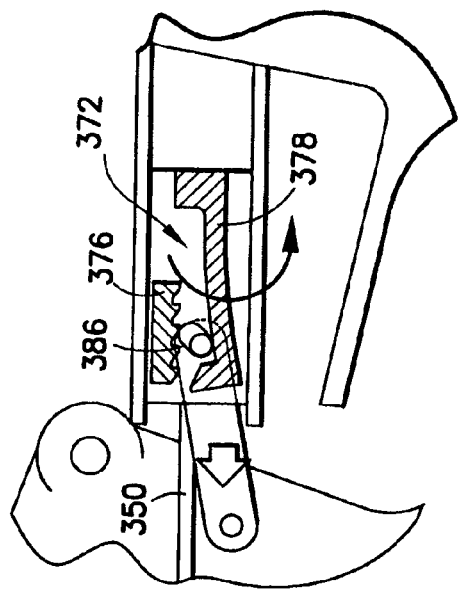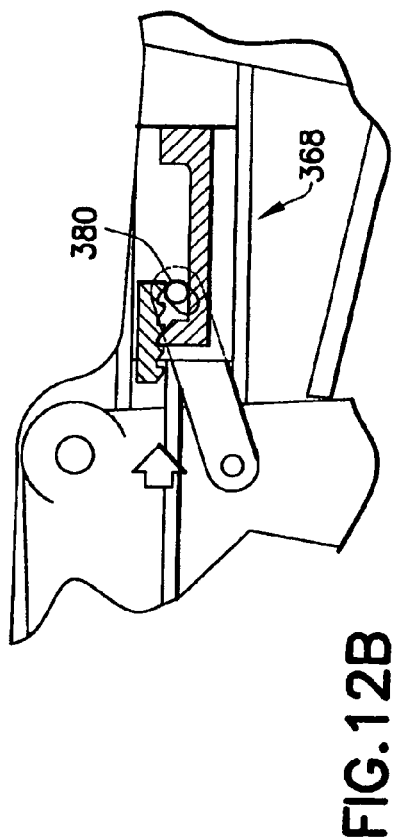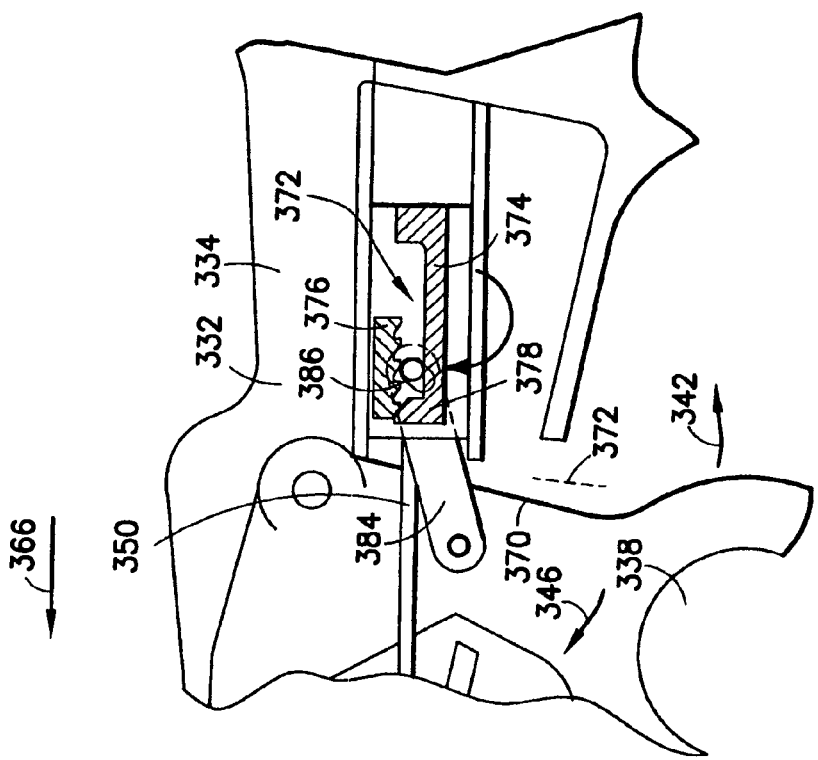

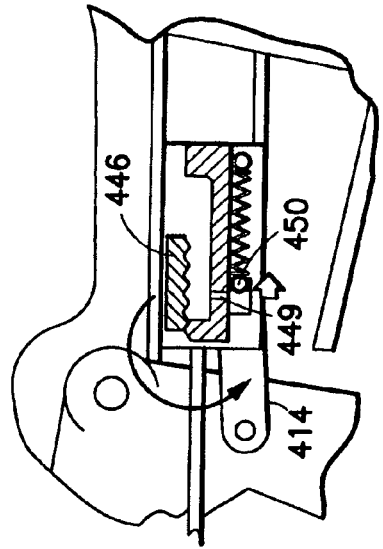
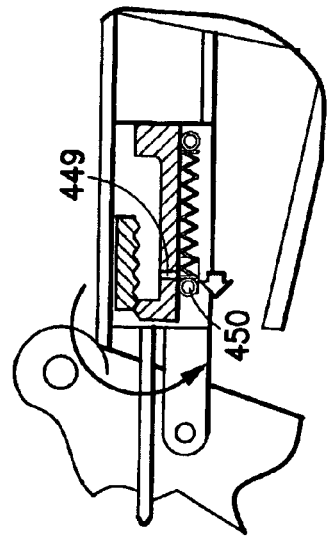
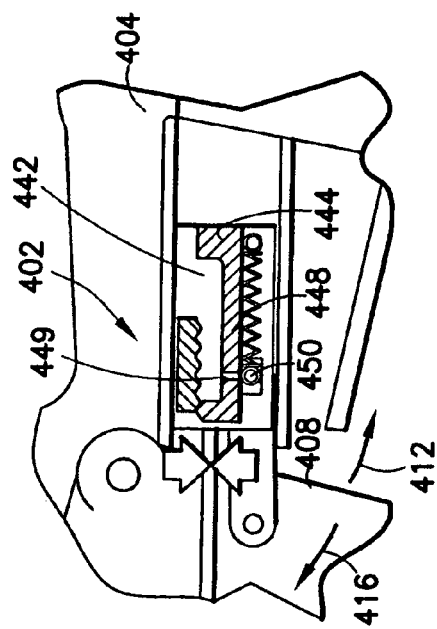
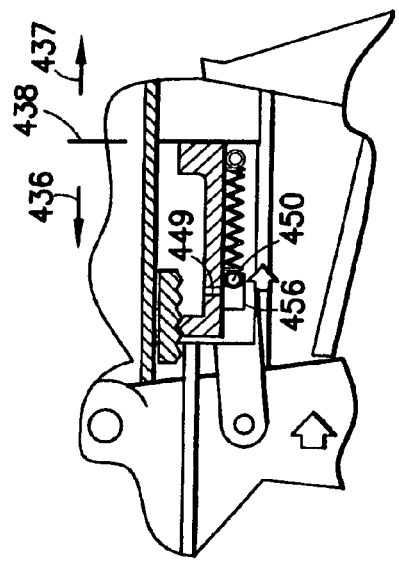

ONE-HAND LOCKING AND RELEASING HANDHELD MEDICAL INSTRUMENT

This application claims the benefit of U.S. Provisional Application Ser. No. 60/419,582 filed on Oct. 21, 2002.

BACKGROUND

1. Field of the Exemplary Embodiments

The exemplary embodiments of the present invention relate to a manipulating devices, and more particularly to lockable medical manipulating devices with an auto release feature.

2. Brief Description of Earlier Related Developments

Minimally invasive surgical procedures are being used with increasing regularity. These procedures are performed with minimally invasive surgical instruments which include a tool on the end of an elongated support tube opposite a handle. Access to the surgical site is provided by a trocar which is used to puncture and insert a cannula or hollow tube through the patient's skin and muscle tissue. The tool of the surgical instrument is positioned at the surgical site after being inserted through the cannula. The surgeon then manipulates a lever or other actuator on the handle to perform the surgical operation. This procedure is carried out while viewing the surgical site on a video monitor. Minimally invasive surgical procedures of this type offer substantial benefits to the patient in terms of reduced postoperative pain, reduced recovery time, and lower cost. In a variety of medical devices used for a diversity of surgical or non-surgical procedures, devices are designed with a dedicated handle or proximal end and a distal or actuation end. Typically medical device handles prescribe how they will be held in the hand by the layout of their handle shape or position of finger loops. In instruments that contain loops, such as can be found in scissors type devices or grasping type devices, the loops are used for opening and closing the end effector, whether that is a scissors, grasper, clamp or similar device. In medical devices and more specifically minimally invasive or laparoscopic devices, a wide variety of handles, levers or loops may be used in a variety of combinations. In one example, a finger-looped device may be employed as part of the instrument handle in combination with two or more finger or thumb elements that perform the same or similar functions, such as clamping and releasing jaw members of the medical device. One problem arises when the operator desires the jaw members to remain clamped while switching between instruments or between finger elements. Another problem arises when the operator desires to release the jaw members without actuating a separate element or without excessive movement of the operators fingers, as where the operator is at the extremes of motion or beyond their comfort range. Accordingly, there is a desire to provide a locking and releasing apparatus for operating medical devices that locks and releases without actuating a separate element or without excessive movement of the operators fingers.

SUMMARY OF THE EXEMPLARY EMBODIMENTS

In accordance with one exemplary embodiment of the present invention, a locking and releasing apparatus for operating a medical device is provided having a handle and a lever member coupled to the handle for grasping engagement by an operator. The lever member is moveable in opposite directions relative to the handle. A locking and release mechanism operably connects the lever member to a force transmitting member for operating the medical device at a location distant from the handle. The locking and release mechanism locks movement of the force transmitting member in one direction after movement of the lever member in a locking direction. The locking and release mechanism releases movement of the force transmitting member in the one direction after opposite movement of the lever member in a releasing direction. The lever member operates the locking and release mechanism for releasing the movement of the force transmitting member in the one direction substantially upon changing movement of the lever member from the locking to the releasing direction.

In accordance with another embodiment of the present invention, a locking and releasing apparatus for operating a medical device is provided having a handle and a lever member mounted on the handle for grasping engagement by an operator. The lever member is moveable in opposite first and second directions relative to the handle over a predetermined range of motion. A locking mechanism operably connects the lever member to a force transmitting member for operating the medical device at a location distant from the handle. A release mechanism operably connects to the lever member. The locking mechanism locks movement of the force transmitting member at a locking position located over at least part of the range of motion of the lever member after movement of the lever member in the first direction. Changing the direction of movement of the lever member from the first direction where the lever member is at the locking position causes the release mechanism to release movement of the force transmitting member.

In accordance with another embodiment of the present invention, a one hand locking and releasing apparatus for operating a medical device is provided having a handle and a finger loop mounted on the handle for receiving a finger of an operator. First and second lever members are mounted on the handle for grasping engagement by other fingers of the operator. At least one of the lever members is mounted on the handle for movement in first and second directions relative to the finger loop. A locking and release mechanism operably connects at least one of the first and second lever members to a force transmitting member for operating the medical device at a location distant from the handle. The locking and release mechanism is actuated for locking movement of the force transmitting member by movement of the at least one of the lever members in the first direction. The locking and release mechanism is actuated for releasing movement of the force transmitting member by movement of the at least one of the lever members in the second direction, the at least one of the lever members actuating the locking and release mechanism for releasing movement substantially upon changing direction of movement of the at least one of the lever members from the first direction to the second direction. In the course of operating the medical device, the operator can reposition his fingers between the first and second lever members with rotation of the finger within the finger loop.

BRIEF DESCRIPTION OF THE DRAWINGS

FIGS. 4A, 4B and 4C are further schematic section views of the locking and releasing apparatus of the device shown in FIG. 3;

FIGS. 8A, 8B and 8C are further schematic section views of the locking and releasing apparatus of the device shown in FIG. 7;

FIGS. 10A, 10B and 10C are further schematic section views of the locking and releasing apparatus of the device shown in FIG. 9;

FIGS. 12A, 12B and 12C are further schematic section views of the locking and releasing apparatus of the device shown in FIG. 11;

FIGS. 14A, 14B, 14C and 14D are further schematic section views of the locking and releasing apparatus of the device shown in FIG. 13.

DETAILED DESCRIPTION OF THE EXEMPLARY EMBODIMENTS

Figure 1:
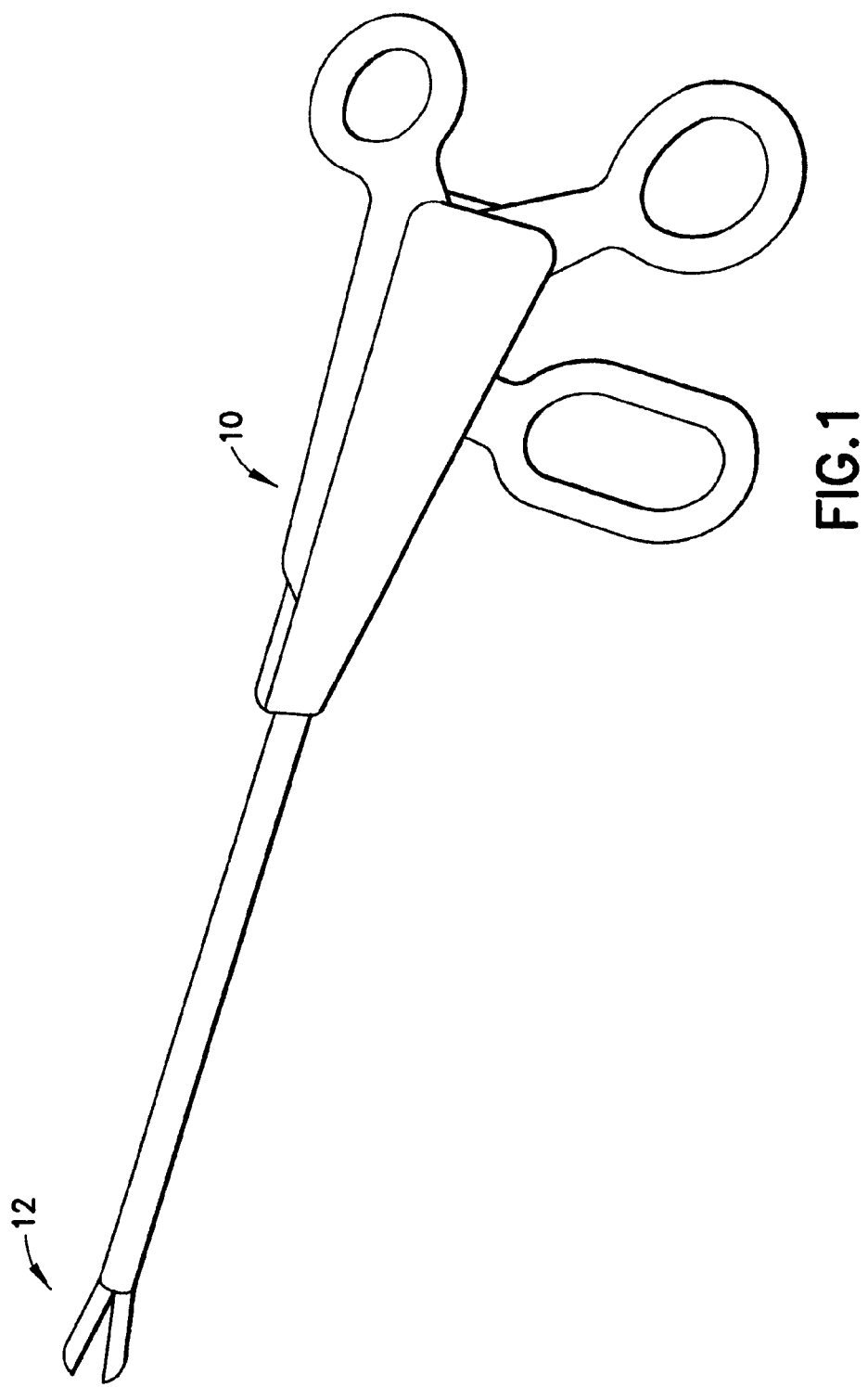
FIG. 1 is a diagrammatic perspective view illustrating a manipulating device incorporating features of an exemplary embodiment of the present invention.
Figure 2:
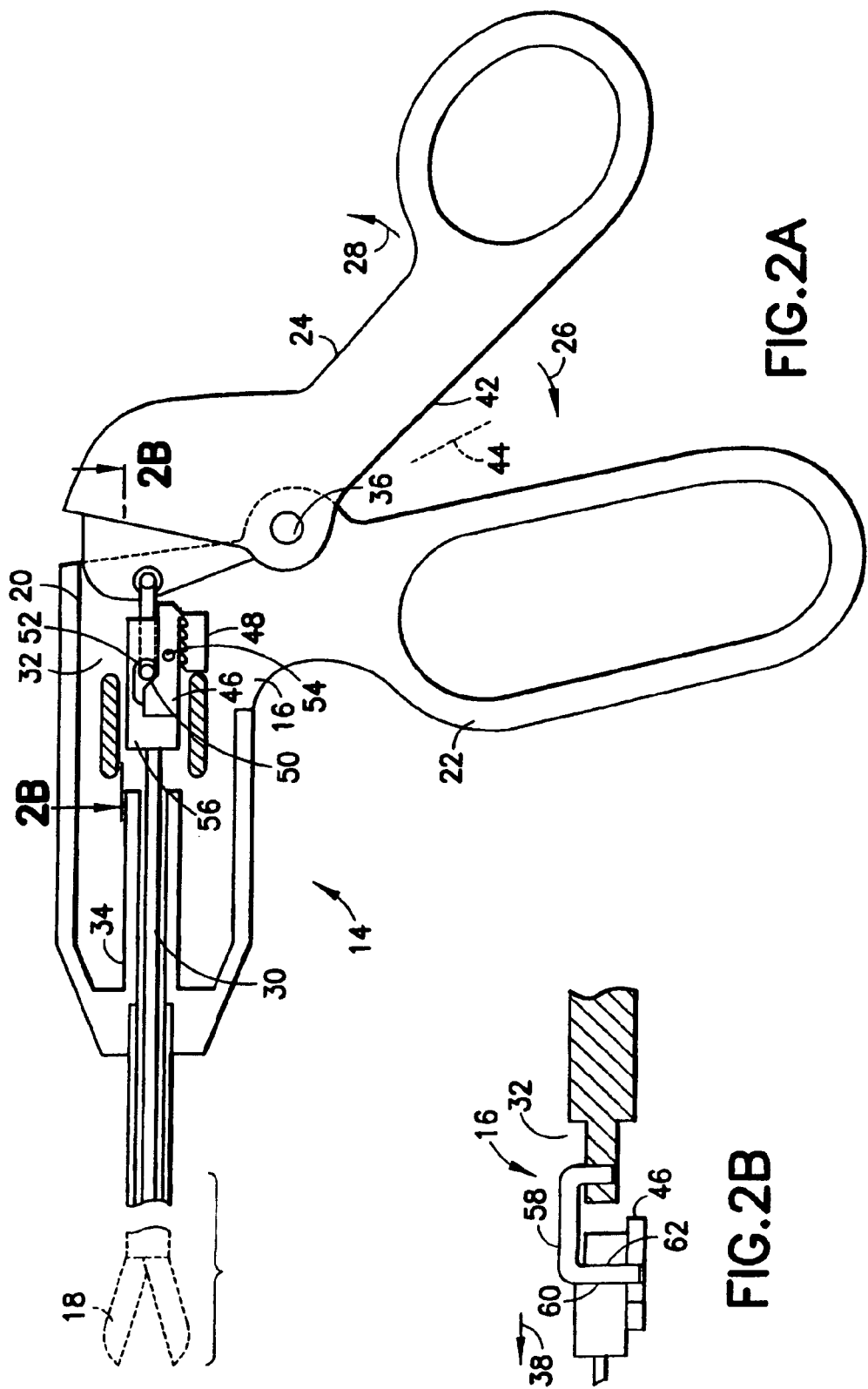
FIG. 2A is a schematic elevation view of one embodiment of a locking and releasing apparatus of the device in FIG. 1.
FIG. 2B is a schematic plan view of the locking and release mechanism of the locking and releasing apparatus in FIG. 2A.

Referring now to FIG. 1, there is shown a diagrammatic perspective view illustrating a locking and releasing apparatus 10 for operating a device 12 according to one exemplary embodiment of the present invention. Device 12 may be a scissors, grasper, clamp or other similar device. In alternate embodiments, any suitable device may be applied, including for example a medical device. Referring also to FIGS. 2A and 2B, there is shown a schematic section view of one embodiment of a locking and releasing apparatus 14 for operating a medical device according to the exemplary embodiments of the present invention. Although the exemplary embodiments of the present invention will be described with particular reference to the embodiments of a medical manipulating device, as shown in the drawings, it should be understood that the present invention can be embodied in any suitable manipulating device and in many alternate forms of embodiments. In addition, any suitable size, shape or type of elements or materials could be used.

Referring again to FIG. 2A, there is shown a schematic section view of one embodiment of a manipulating apparatus, in this case a locking and releasing apparatus 14, for operating medical device 18 (substantially similar to device 12 described above) according to an exemplary embodiment of the present invention. Referring also to FIG. 2B, there is shown a schematic section view of a locking and release mechanism 16 of the locking and releasing apparatus 14 from FIG. 2A. Locking and releasing apparatus 14 for operating medical device 18 includes a handle 20, a finger loop 22 integral with the handle 20 for receiving a finger, such as for example the thumb or index finger of an operator, and lever member 24 mounted on the handle 20 for grasping engagement by finger(s) of the operator. Lever member may also incorporate a finger loop. In alternate embodiments, more or fewer lever members may be used. The finger loop 22 and/or lever member 24 is generally adapted to receive any suitable finger, such as a thumb, of the operator. Lever member 24 is pivotally mounted on the handle 20 for movement between a first or locking direction 26 and a second or releasing direction 28. Lever member 24 is moveable in opposite first and second directions 26, 28 relative to the handle 16 over a predetermined range of motion. A force transmitting member termed a pull rod 30 extends away from a locking and release mechanism 32, and from the finger loop 22 and from lever member 24, passing through a guide cannula 34. Force transmitting member 30, through locking and release mechanism 32 operably connects the lever member 24 to the medical device 18 for operating the medical device 18 which is located distant from the handle. Force transmitting member 30 may be of any suitable construction including, by way of example, wire, chain, a linkage, and the like. Lever member 24 is pivotally attached, as by pin 36, to the handle 16. In alternate embodiments, linear instead of rotary or combinations of linear and rotary arrangements and/or constraints may be applied to between lever member 24 and handle 16. Movement of lever member 24 from its initial positions farthest from the finger loop 22 to extended position nearest to the finger loop results in that the pull rod 30 is drawn in a direction away from the medical device 18 with appropriate actuation of the medical device 18. In an opposite manner, with movement of the lever member 24 from extended, latched or clamped position toward its initial or unclamped position, pull rod 30 is advanced in a direction toward the medical device 18 with its appropriate actuation. Locking and release mechanism 32 operably connects lever member 24 to force transmitting member 30 for operating the medical device 18 at a location distant from the handle. Locking and release mechanism 32 locks movement of the force transmitting member in one direction 38 after movement of the lever member 24 in locking direction 26. Locking and release mechanism 32 releases movement of the force transmitting member 30 in the one direction 38 after opposite movement of the lever member 24 in a releasing direction 28. Lever member 24 operates the locking and release mechanism 32 releasing the movement of the force transmitting member 30 in the one direction 38 substantially upon changing movement of the lever member 24 from the locking 26 to the releasing direction 28. Locking mechanism 32 locks movement of the force transmitting member 30 at a locking position 40 (see FIG. 2B), located over at least part of the range of motion 42, 44 of lever member 24 after movement of the lever member in first direction 26. Changing the direction of movement of the lever member 24 from first direction 26 where the lever member is at a locking position causes the release mechanism 32 to release movement of force transmitting member 30 (see FIG. 2B). Releasing direction 28 is substantially opposite of locking direction 26. Locking and release mechanism 32 has a pawl 46 and a rack 48 coupled to either force transmitting member 30 or handle 16 respectively. Pawl 46 engages the rack 48 after movement of lever member 24. Pawl 46 disengages the rack 48 after opposite movement of lever member 24. Pawl 46 has camming surface 50. Camming surface 50 is engaged by pin 52 through relative movement between lever member 24 and pawl 46. Locking and release mechanism 32 further comprises a spring 54 biasing pawl 46 to engage rack 48. Force transmitting member 30 is coupled to sliding block 56.

Sliding block 56 is constrained to slide relative to frame 16. Rack 48, in the embodiment shown is grounded to frame 16. Pawl 46 is pivotally coupled to sliding block 56. Link 58 is pivotally coupled to lever 24. Link 58 has pin 60 which slides in slot 62 of sliding block 56. Pin 60 in combination with slot 62 enables camming surface 50 to be engaged by pin 60 through relative movement between lever member 24 and pawl 46 through link 58 resulting in pawl 46 engaging rack 48 after movement of lever member 24.

As noted before, when the operator, with a finger in loop 22 moves lever 24 (for example with another finger on the same hand) in locking direction 26, the block 56 and pawl are correspondingly moved in the locking direction. This causes the pawl to ratchet block 56, and hence rod 30. The operator can effect release of the ratchet (block 56, rod 30) at any desired location throughout the range of motion of the ratchet. The operator effects release by merely reversing the direction of movement of lever 24. Indeed, as lever 24 also incorporates a finger loop, the operator effects release of the ratchet (and rod 30) merely by changing the direction of movement of the finger operating lever 24 from the locking direction 26 to the unlocking direction 28. This reversal causes pin 52 to engage cam 50 and, upon overcoming the spring bias, lift the pawl from the rack. The lost motion gap between the pin 52 and cam 50 remains constant throughout the range of movement of the ratchet. Hence, release of the locking and release apparatus occurs with substantially the same amount of movement regardless of the extent to which the apparatus has been ratcheted.

Figure 3:
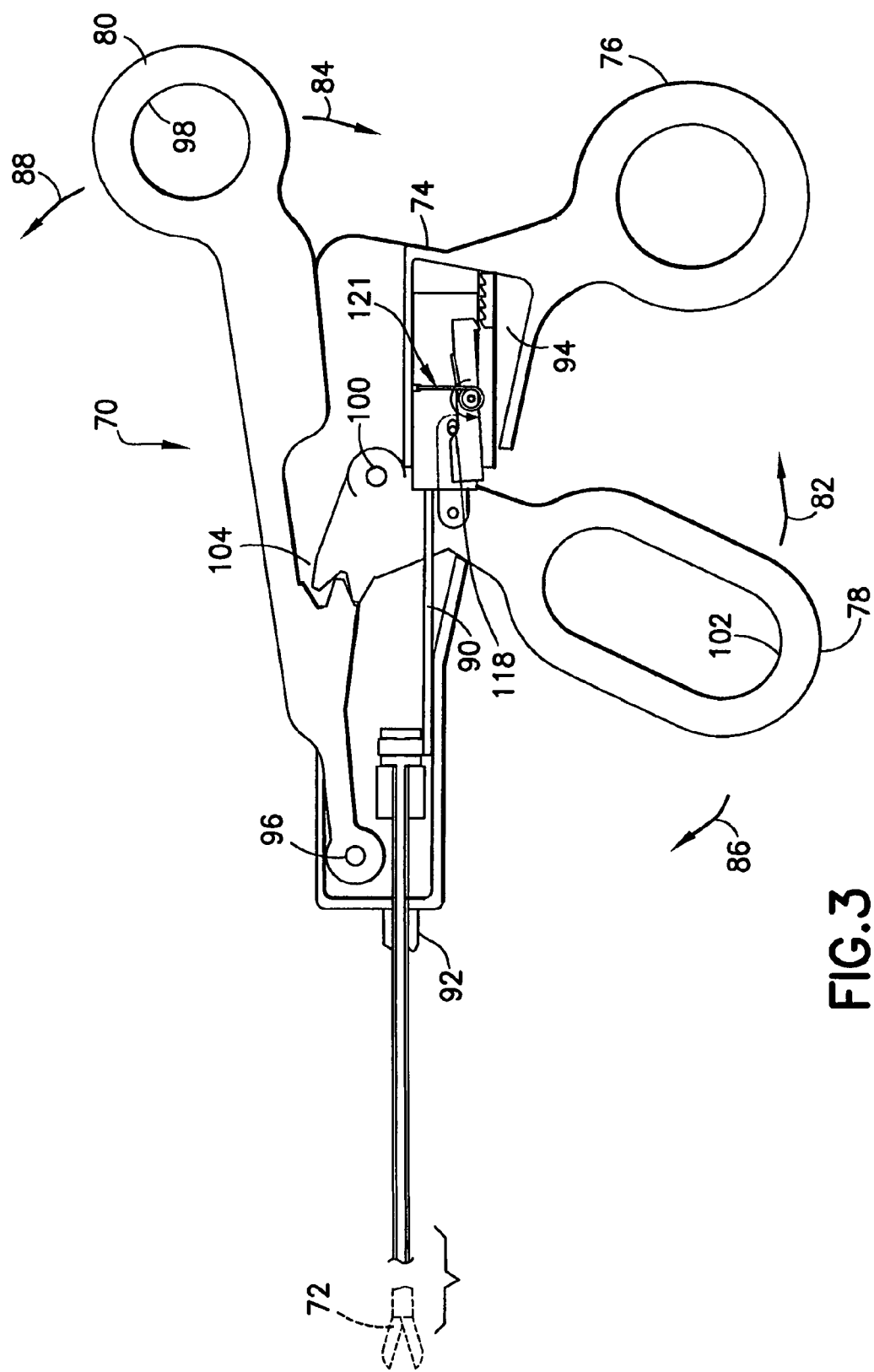
FIG. 3 is a schematic elevation view of another exemplary embodiment of the device.

Referring now to FIG. 3, there is shown a schematic section view of another exemplary embodiment of a one hand locking and releasing apparatus 70 for operating a medical device. Referring also to FIGS. 4A, 4B and 4*c* there is shown a schematic section view of a locking and release mechanism 94 of the locking and releasing apparatus 70 in FIG. 3. One hand locking and releasing apparatus 70 for operating a medical device 72 includes a handle 74, a finger loop 76 integral with the handle for receiving a finger, such as for example the thumb of an operator, and first and second lever members, 78, 80, respectively, mounted on the handle 74 for grasping engagement by fingers of the operator. In alternate embodiments, more or fewer lever members may be used. Each of the lever members 78, 80 may also incorporate a finger loop as shown. The finger loop 76 is generally adapted to receive any suitable finger, such as a thumb, of the operator and may facilitate a change in hand position without losing control of the device. The lever members 78, 80 are pivotally mounted on the handle 74 for movement between a first or locking direction 82, 84 and a second or releasing direction 86, 88. Lever members 78, 80 are moveable in opposite first and second directions relative to the handle over a predetermined range of motion. A force transmitting member termed a pull rod 90 extends away from a locking and release mechanism 94 and from the finger loop 76 and from the lever members 78, 80 and, passing through a guide cannula 92. Force transmitting member 90 through locking and release mechanism 94 operably connects the lever member 80 to the medical device 72 for operating the medical device which is located distant from the handle. Force transmitting member 90 may be of any suitable construction including, by way of example, wire, chain, a linkage, and the like. The operator can reposition his fingers between the lever members 78, 80 with rotation of his thumb within the finger loop 76. Lever member 80 is pivotally attached, as by pin 96, to the handle 74. An upper finger loop 98 may be integral with lever member 80. Lever member 78 is also pivotally attached by a pin 100 to handle 74. Finger loop 102 may be integral with lever member 78. An interengagement construction 104 may be provided between lever members 78, 80 such that they move in a coordinated manner in directions 82, 84 and 86, 88 and first and second positions. Embodiments of such an interengagement construction are disclosed in U.S. patent application Ser. No. 10/625,965, filed Jul. 24, 2003, which is hereby incorporated by reference in its entirety. In alternate embodiments, alternate interengagement mechanisms may be provided, such as where directions 88 and 82 are coordinated for example. In alternate embodiments, linear instead of rotary or combinations of linear and rotary arrangements and/or constraints may be applied to between lever members 78, 80. In alternate embodiments, lever members 78, 80 may be each coupled to locking and releasing mechanism 94. Movement of lever members 78, 80 from their initial positions farthest from the finger loop 76 to extended positions nearest to the finger loop results in that the pull rod 90 is drawn in a direction away from the medical device 72 with appropriate actuation of the medical device 72. In an opposite manner, with movement of the lever members 78, 80 from extended, latched or clamped positions toward their initial or unclamped positions, pull rod 90 is advanced in the direction toward the medical device 72 with its appropriate actuation.

Referring also to FIGS. 4A, 4B and 4C there is shown schematic section views of the embodiment shown in FIG. 3. Locking and release mechanism 94 operably connects lever member 78 to force transmitting member 90 for operating the medical device 72 at a location distant from the handle. Locking and release mechanism 94 locks movement of the force transmitting member in one direction 106 after movement of the lever member 78 in locking direction 82. Locking and release mechanism 94 releases movement of the force transmitting member 90 in the one direction 106 after opposite movement of the lever member 78 in a releasing direction 86. Lever member 78 operates the locking and release mechanism 94 releasing the movement of the force transmitting member 90 in the one direction 106 substantially upon changing movement of the lever member 78 from the locking 82 to the releasing direction 86. Locking mechanism 94 locks movement of the force transmitting member 90 at a locking position 108 (see FIG. 4B), located over at least part of the range of motion 110, 112 of lever member 78 after movement of the lever member in first direction 82. Changing the direction of movement of the lever member 78 from first direction 82 where the lever member is at a locking position causes the release mechanism 94 to release movement of force transmitting member 90 (see FIG. 4C). Releasing direction 86 is substantially opposite of locking direction 82. Locking and release mechanism 94 has a pawl 114 and a rack 116 coupled to either force transmitting member 78 or handle 74 respectively. Pawl 114 engages the rack 116 after movement of lever member 78. Pawl 114 disengages the rack 116 after opposite movement of lever member 78. Pawl 114 has camming surface 118. Camming surface 118 is engaged by pin 120 through relative movement between lever member 78 and pawl 114. Locking and release mechanism 94 further comprises a spring 121 biasing pawl 114 to engage rack 116. Force transmitting member 90 is coupled to sliding block 122. Sliding block 122 is constrained to slide relative to frame 74. Rack 116, in the embodiment shown is grounded to frame 74. Pawl 114 is pivotally coupled to sliding block 122. Link 124 is pivotally coupled to lever 78. Link 124 has pin 120 which slides in slot 126 of sliding block 122. Pin 120 in combination with slot 126 enables camming surface 118 to be engaged by pin 120 through relative movement between lever member 78 and pawl 114 through link 124 resulting in pawl 114 engaging rack 116 after movement of lever member 78. As seen in FIGS. 4A–4C, release of the transmitting member 90, is readily performed in a manner similar to that described before by reversing direction of motion of either lever member 78, 80.

Figure 5:
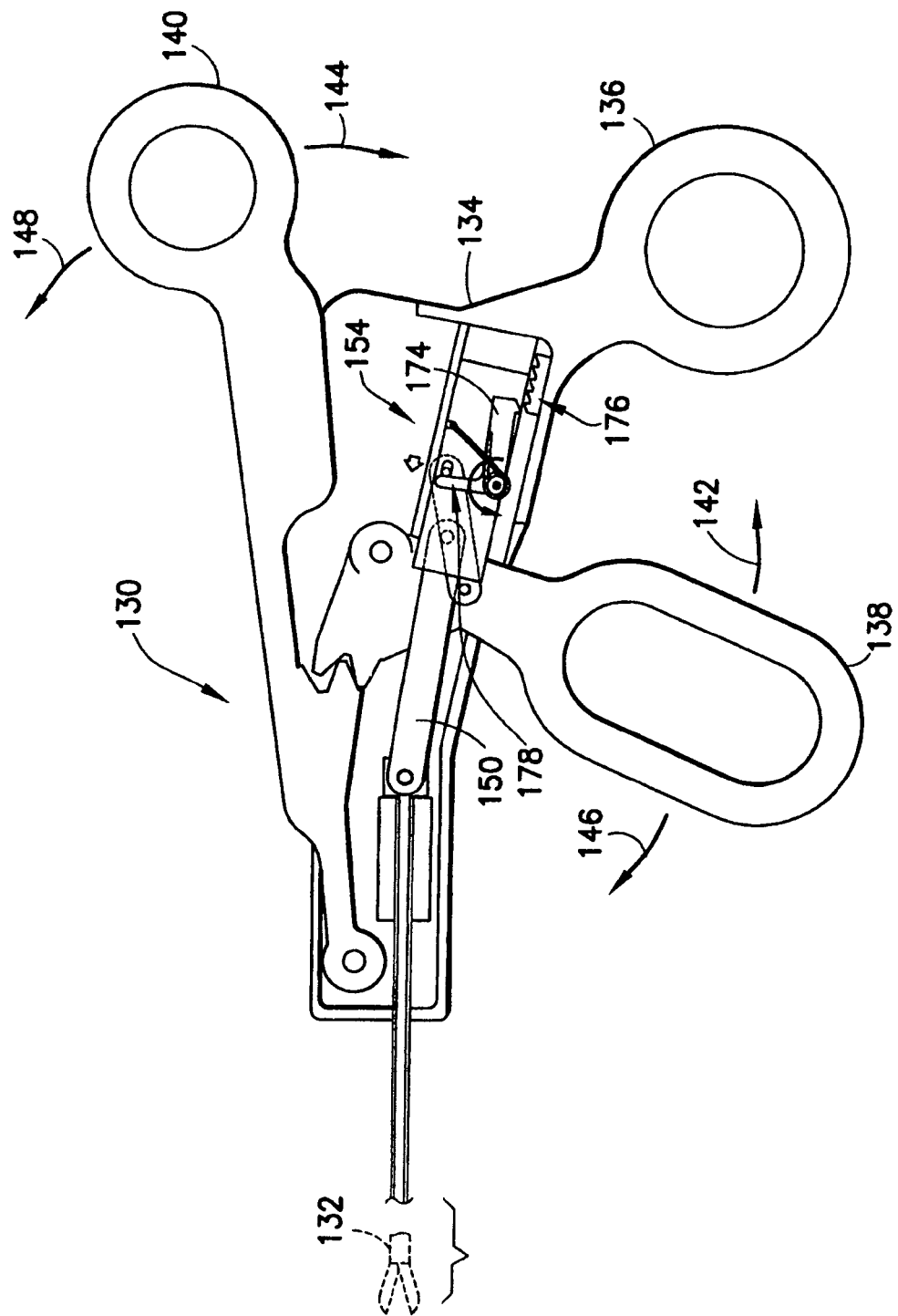
FIG. 5 is a schematic elevation view of yet another exemplary embodiment of the device.
Figure 6A:
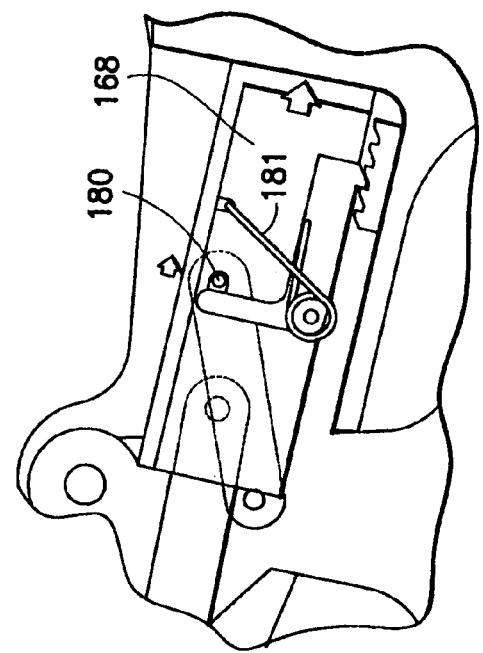
FIGS. 6A, 6B and 6C are further schematic section views of the locking and releasing apparatus of the device shown in FIG. 5.
Figure 6B:
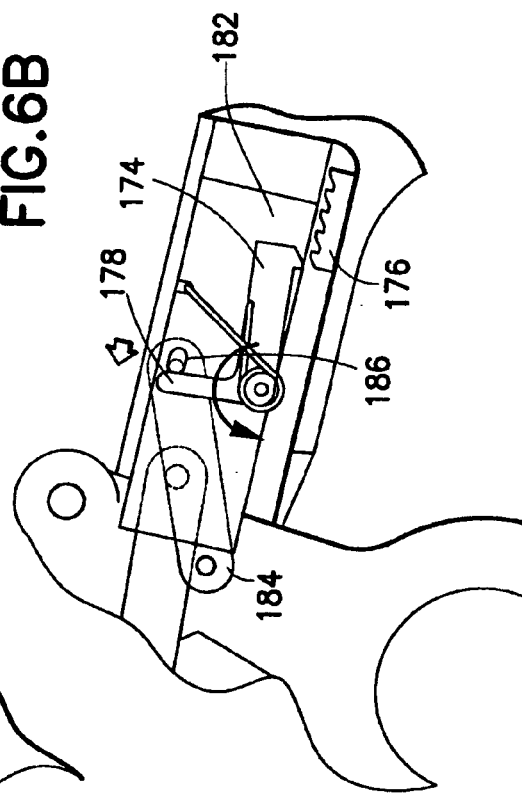
Figure 6C:
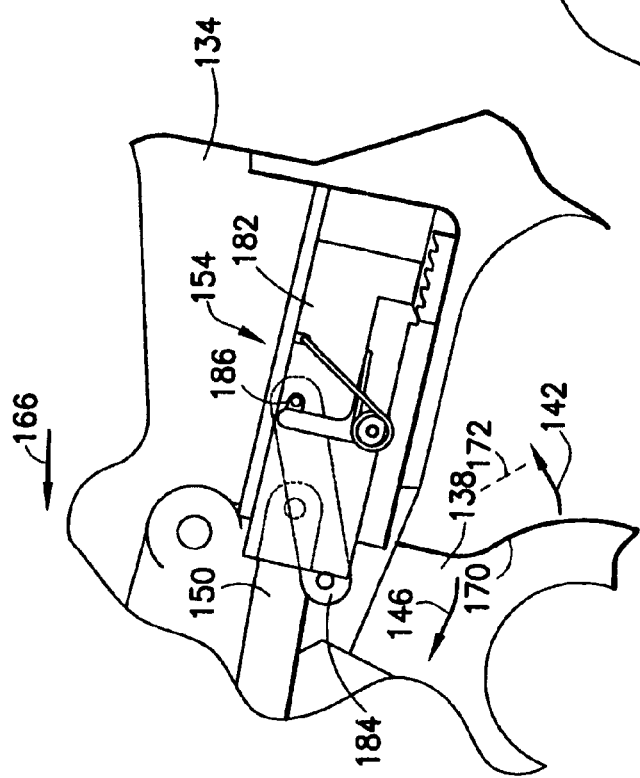

Referring now to FIG. 5, there is shown a schematic section view of another exemplary embodiment of a one hand locking and releasing apparatus 130 for operating a medical device. Referring also to FIGS. 6A, 6B and 6C there is shown a schematic section view of a locking and release mechanism 154 of the locking and releasing apparatus 130 from FIG. 5. One hand locking and releasing apparatus 130 for operating a medical device 132 similarly includes a handle 134, a finger loop 136 integral with the handle and first and second lever members, 138, 140, respectively, mounted on the handle 134. The lever members 138, 140, which may also incorporate respective finger loops as shown, are pivotally mounted on the handle 134 for movement between a first or locking direction 142, 144 and a second or releasing direction 146, 148. Lever members 138, 140 are moveable in opposite first and second directions relative to the handle over a predetermined range of motion. A force transmitting member termed a pull rod 150 extends away from a locking and release mechanism 154. Force transmitting member 150 through locking and release mechanism 154 operably connects the lever member 138 to the medical device 132 for operating the medical device. Lever members 138, 140 are pivotally attached to the handle. An interengagement construction may be provided between lever members 138, 140 such that they move in a coordinated manner in directions as previously described. Movement of lever members 138, 140 from their initial positions farthest from the finger loop 136 to extended positions nearest to the finger loop results in that the pull rod 150 is drawn in a direction away from the medical device 132 with appropriate actuation of the medical device 132. In an opposite manner, with movement of the lever members 138, 140 from extended, latched or clamped positions toward their initial or unclamped positions, pull rod 150 is advanced in the direction toward the medical device 132 with its appropriate actuation.

Referring also to FIGS. 6A, 6B and 6C there is shown schematic section views of the embodiment shown in FIG. 5 of a locking and releasing apparatus for operating a medical device. Locking and release mechanism 154 operably connects lever member 138 to force transmitting member 150 for operating the medical device 132 at a location distant from the handle. Locking and release mechanism 154 locks movement of the force transmitting member in one direction 166 after movement of the lever member 138 in locking direction 142. Locking and release mechanism 154 releases movement of the force transmitting member 150 in the one direction 166 after opposite movement of the lever member 138 in a releasing direction 146. Lever member 138 operates the locking and release mechanism 154 releasing the movement of the force transmitting member 150 in the one direction 166 substantially upon changing movement of the lever member 138 from the locking 142 to the releasing direction 146. Locking mechanism 154 locks movement of the force transmitting member 150 at a locking position 168 (see FIG. 6B), located over at least part of the range of motion 170, 172 of lever member 138 after movement of the lever member in first direction 142. Changing the direction of movement of the lever member 138 from first direction 142 where the lever member is at a locking position causes the release mechanism 154 to release movement of force transmitting member 150 (see FIG. 6C). Releasing direction 146 is substantially opposite of locking direction 142. Locking and release mechanism 154 has a pawl 174 and a rack 176 coupled to either force transmitting member 150 or handle 134 respectively. Pawl 174 engages the rack 176 after movement of lever member 138. Pawl 174 disengages the rack 176 after opposite movement of lever member 138. Pawl 174 has lever surface or camming surface 178. Lever surface or camming surface 178 is engaged by pin 180 through relative movement between lever member 138 and pawl 174. Locking and release mechanism 154 further comprises a spring 181 biasing pawl 174 to engage rack 176. Force transmitting member 150 is coupled to sliding block 172. Sliding block 172 is constrained to slide relative to frame 134. Rack 176, in the embodiment shown is grounded to frame 134. Pawl 174 is pivotally coupled to sliding block 182. Link 184 is pivotally coupled to lever 138. Link 184 has pin 180 which slides in slot 186 of sliding block 182. Pin 180 in combination with slot 186 enables lever surface or camming surface 178 to be engaged by pin 180 through relative movement between lever member 138 and pawl 174 through link 184 resulting in pawl 174 engaging rack 176 after movement of lever member 138.

Figure 7:
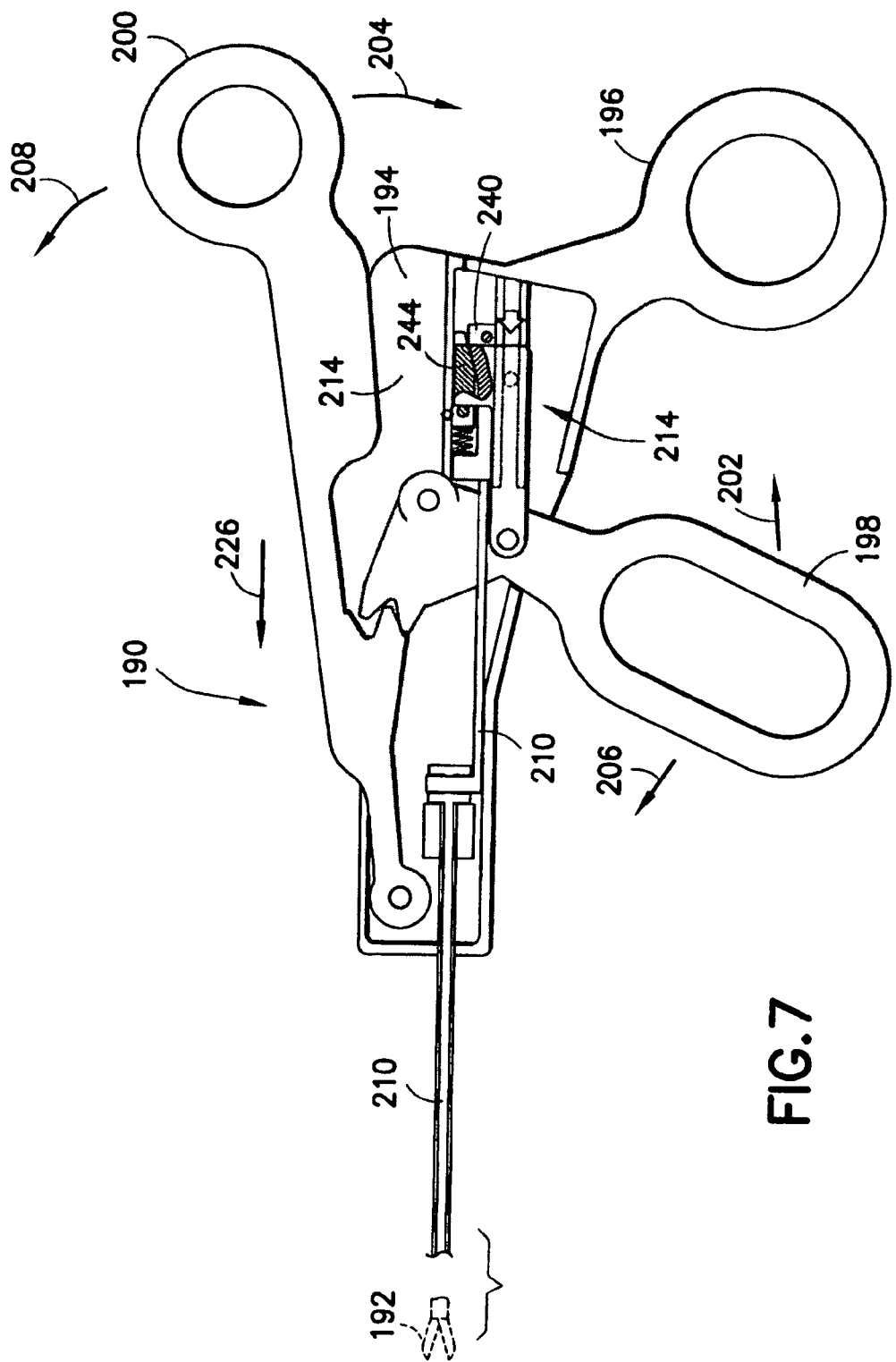
FIG. 7 is a schematic elevation view of yet another exemplary embodiment of the device.

Referring now to FIG. 7, there is shown a schematic section view of another exemplary embodiment of a one hand locking and releasing apparatus 190 for operating a medical device. Referring also to FIGS. 8A, 8B and 8C there is shown a schematic section view of a locking and release mechanism 214 of the locking and releasing apparatus 190 from FIG. 7. One hand locking and releasing apparatus 190 for operating a medical device 192 similarly includes a handle 194, a finger loop 196 integral with the handle and first and second lever members, 198, 200 pivotally mounted on the handle 194 for movement between a first or locking direction 202, 204 and a second or releasing direction 206, 208. An interengagement construction may be provided. Movement of lever members 198, 200 from their initial positions farthest from the finger loop to extended positions nearest to the finger loop results in that the pull rod 210 is drawn and in an opposite manner, with movement of the lever members 198, 200 from extended, latched or clamped positions toward their initial or unclamped positions, pull rod 210 is advanced. As seen best in FIGS. 8A–8C, locking and release mechanism 214 operably connects lever member 198 to force transmitting member 210 for operating a medical device at a location distant from the handle. Locking and release mechanism 214 locks movement of the force transmitting member in one direction 226 after movement of the lever member 198 in the locking direction. Locking and release mechanism 214 releases movement of the force transmitting member in the one direction after opposite movement of the lever member in a releasing direction. Lever member 198 operates the locking and release mechanism releasing the movement of the force transmitting member in the one direction substantially upon changing movement of the lever member from the locking to the releasing direction. Locking mechanism 214 locks movement of the force transmitting member 210 at a locking position 228 (see FIG. 8B), located over at least part of the range of motion 230, 232 of lever member 198 after movement of the lever member in the first direction. Changing the direction of movement of the lever member 198 from the first direction where the lever member is at a locking position causes the release mechanism 214 to release movement of force transmitting member 210 (see FIG. 8C). Releasing direction 266 is substantially opposite of locking direction 202. The locking and release mechanism 214 comprises a first wedge 240 coupled to the force transmitting member and a second wedge 244 slidingly coupled to the first wedge. Lever member 198 engages the first wedge 240 or the force transmitting member in the locking direction 202 and the second wedge in the unlocking direction 206. The lever member engages the second wedge in the releasing direction 206. A spring 246 biases wedging surfaces 248, 250 of the first and second wedges against each other. First wedge 240 and second wedge 244 are constrained to slide relative to frame 134. Pins 249, 251 are coupled to first wedge 240 and second wedge 244 respectively. Pusher link 252 is pivotally coupled to lever 198. Link 252 has dog 254 and pin 256 which slides in slot 258 of the handle. Dog 254 in combination with selective engagement of pins 249, 251 through movement of lever 198 enables frictional locking or unlocking of surfaces 248, 250 through relative movement between lever member 198.

Figure 9:
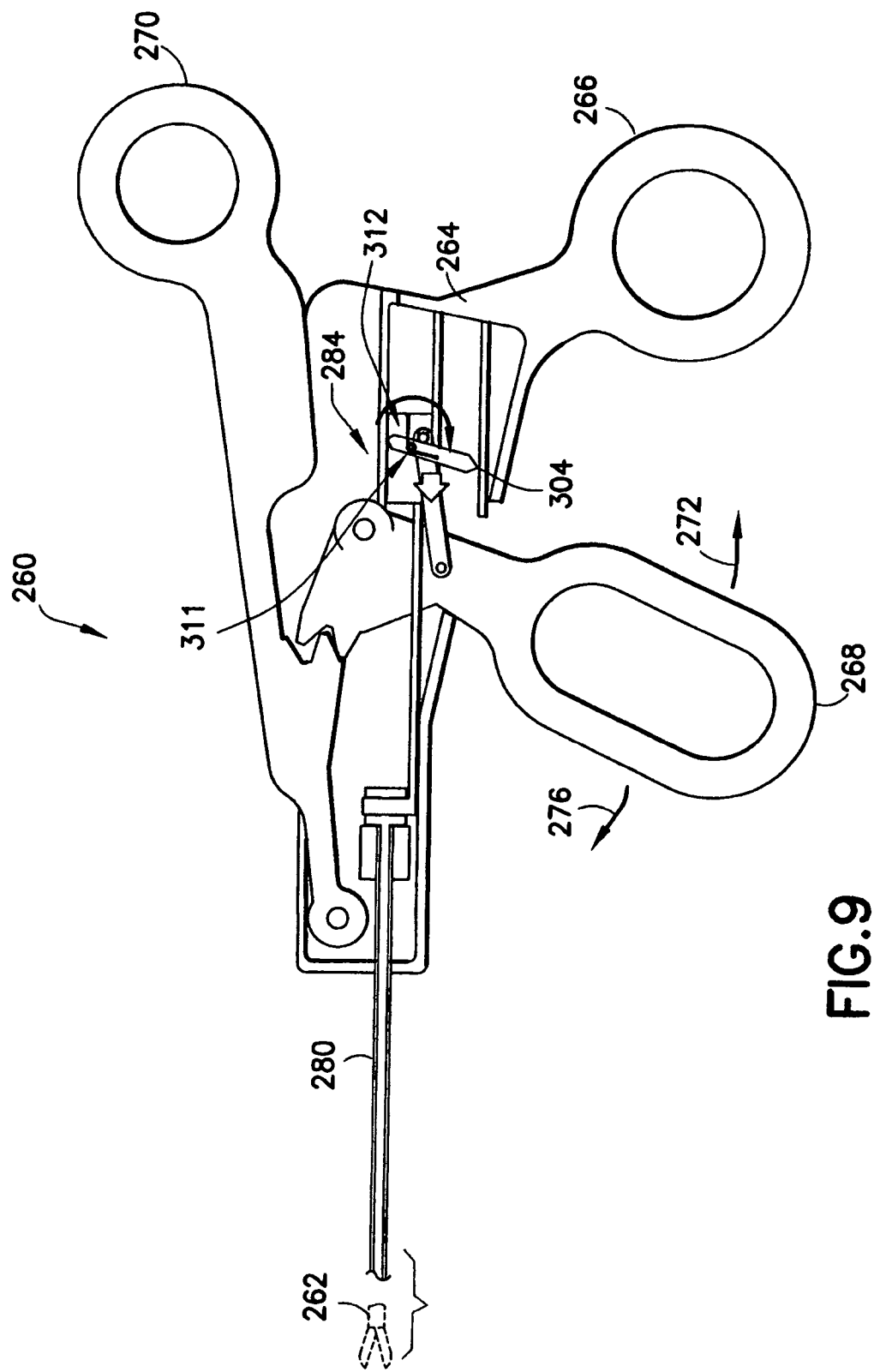
FIG. 9 is a schematic elevation view of yet another exemplary embodiment of the device.

Referring now to FIG. 9, there is shown a schematic section view of yet another exemplary embodiment of a one hand locking and releasing apparatus 260. Referring also to FIGS. 10A, 10B and 10C there is shown a schematic section view of a locking and release mechanism 284 of the locking and releasing apparatus 260 from FIG. 9. One hand locking and releasing apparatus 260 similarly includes a handle 264, a finger loop 266 integral with the handle and first and second lever members, 268, 270 pivotally mounted movement between a first or locking direction 272 a second or releasing direction 276. The lever members are moveable in opposite first and second directions relative to the handle over a predetermined range of motion. A force transmitting member 280 extends away from a locking and release mechanism 284. Force transmitting member 280 through locking and release mechanism 284 operably connects the lever member 268 to the medical device. Locking and release mechanism 284 operably connects lever member 268 to force transmitting member 280 for operating the medical device. Locking and release mechanism 284 locks movement of the force transmitting member in one direction 296 after movement of the lever member 268 in locking direction 272 (see FIGS. 10A–10C). Locking and release mechanism 284 releases movement of the force transmitting member 280 in the one direction 296 after opposite movement of the lever member 268 in a releasing direction 276. Lever member 268 operates the locking and release mechanism 284 releasing the movement of the force transmitting member 280 in the one direction 296 substantially upon changing movement of the lever member 268 from the locking 272 to the releasing direction 276. Locking mechanism 284 locks movement of the force transmitting member 280 at a locking position 298 (see FIG. 10B), located over at least part of the range of motion 300, 302 of lever member 268 after movement of the lever member in first direction 272. Changing the direction of movement of the lever member 268 from first direction 272 where the lever member is at a locking position causes the release mechanism 284 to release movement of force transmitting member 280 (see FIG. 10C). Releasing direction 276 is substantially opposite of locking direction 272. Locking and release mechanism 284 has a cleat wedge 304 coupled to the force transmitting member 280. Lever member 268 engages force transmitting member 280 in the locking direction releases the cleat wedge 304 in the releasing direction. Cleat wedge 304 engages rails 306 after movement of lever member 268 in the clamping direction 272. Cleat wedge 304 disengages rails 306 (see 321 clearance) after opposite movement of lever member 268. Cleat wedge 304 is engaged by pin 310 through relative movement between lever member 268 and cleat wedge 304. Spring 311 biases pawl cleat wedge 304 to engage rails 306. Force transmitting member 280 is coupled to sliding block 312. Sliding block 312 is constrained to slide relative to frame 264. Rails 306 are grounded to frame 264. Cleat wedge 304 is pivotally coupled to sliding block 312. Link 314 is pivotally coupled to lever 268. Link 314 has pin 310 which slides in slot 316 of sliding block 312. Pin 310 in combination with slot 316 enables cleat wedge 304 to be engaged by pin 310 through relative movement between lever member 268 and cleat wedge 304 through link 314 resulting in cleat wedge 304 engaging rail 306 after movement of lever member 268.

Figure 11:
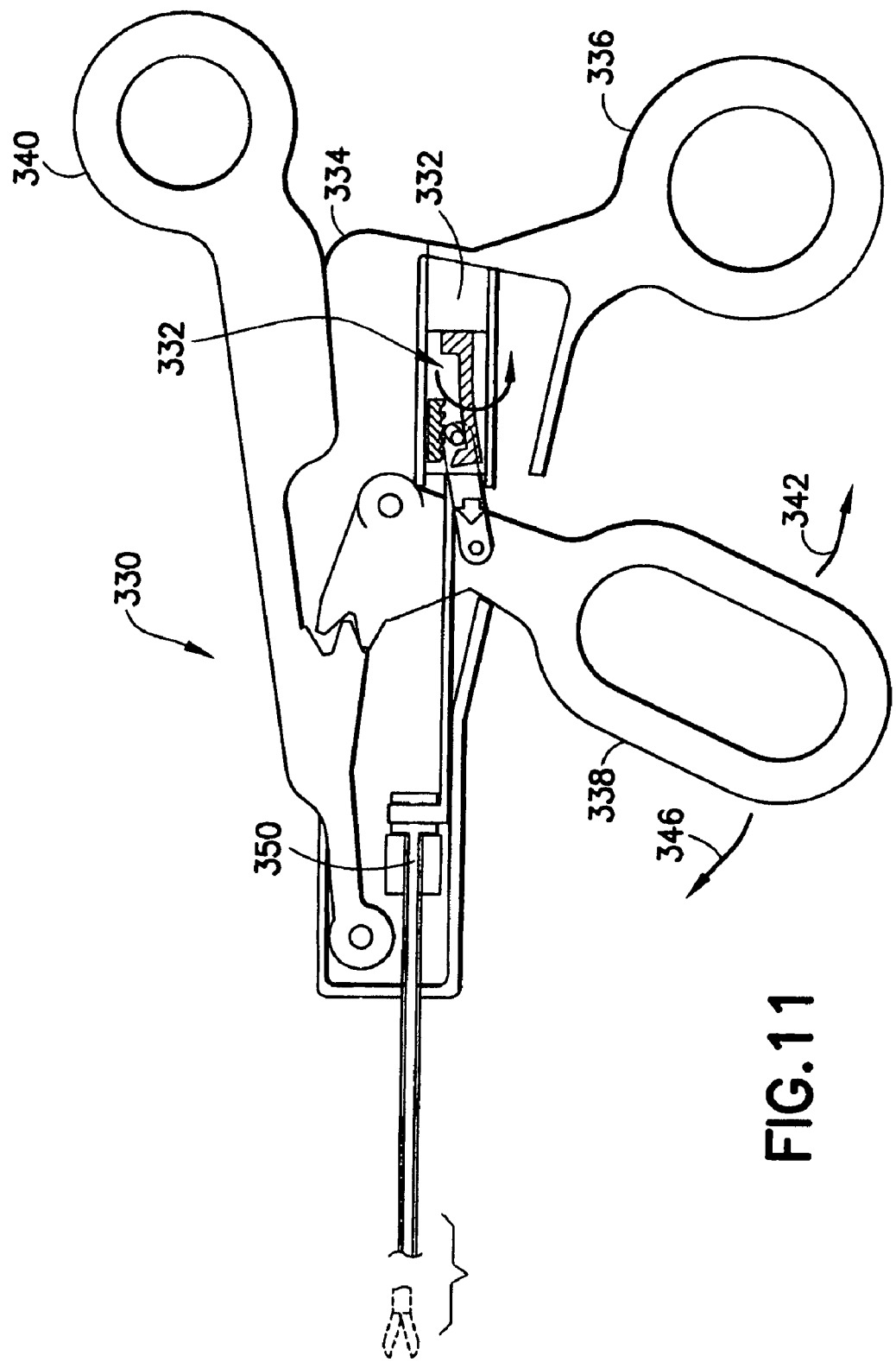
FIG. 11 is a schematic elevation view of yet another exemplary embodiment of the device.

Referring now to FIG. 11, there is shown a schematic section view of still another exemplary embodiment of a one hand locking and releasing apparatus 330. Referring also to FIGS. 12A, 12B and 12C there is shown a schematic section view of a locking and release mechanism 332 of the locking and releasing apparatus 330 from FIG. 11. One hand locking and releasing apparatus 330 similarly includes a handle 334, a finger loop 336 integral with the handle and first and second lever members, 338, 340 pivotally mounted movement between a first or locking direction 342 a second or releasing direction 346. The lever members are moveable in opposite first and second directions relative to the handle over a predetermined range of motion. A force transmitting member 350 extends away from a locking and release mechanism 332. Force transmitting member 350 through locking and release mechanism 334 operably connects the lever member 370 to the medical device. As seen in FIGS. 12A–12C, locking and release mechanism 334 operably connects lever member 338 to force transmitting member 350 for operating the medical device. Locking and release mechanism 334 locks movement of the force transmitting member in one direction 366 after movement of the lever member 370 in locking direction 342. Locking and release mechanism 354 releases movement of the force transmitting member 350 in the one direction 366 after opposite movement of the lever member 338 in a releasing direction 346. Lever member 338 operates the locking and release mechanism 334 releasing the movement of the force transmitting member 350 in the one direction 366 substantially upon changing movement of the lever member 338 from the locking 342 to the releasing direction 346. Locking mechanism 334 locks movement of the force transmitting member 350 at a locking position 368 (see FIG. 12B), located over at least part of the range of motion 370, 372 of lever member 338 after movement of the lever member in first direction 342. Changing the direction of movement of the lever member 338 from first direction 342 where the lever member is at a locking position causes the release mechanism 332 to release movement of force transmitting member 350 (see FIG. 12C). Releasing direction 346 is substantially opposite of locking direction 342. Locking and release mechanism 332 has a pawl 374 and a rack 376 coupled to either force transmitting member 350 or handle 334 respectively. Pawl 374 engages the rack 376 after movement of lever member 338. Pawl 374 disengages the rack 376 after opposite movement of lever member 338. Pawl 374 has flexure section 378. Flexure section 378 is engaged by pin 380 through relative movement between lever member 338 and pawl 374. Flexure section 378 operates as a spring biasing pawl 374 to engage rack 376. Force transmitting member 350 is coupled to sliding block 372. Sliding block 372 is constrained to slide relative to frame 334. Rack 376, in the embodiment shown is grounded to frame 334. Pawl 374 is flexurally coupled to sliding block 382. Link 384 is pivotally coupled to lever 338. Link 384 has pin 380 which slides in slot 386 of sliding block 382. Pin 380 in combination with slot 386 enables flexure section 378 to be engaged by pin 380 through relative movement between lever member 338 and pawl 374 through link 384 resulting in pawl 374 engaging rack 376 after movement of lever member 338.

Figure 13:
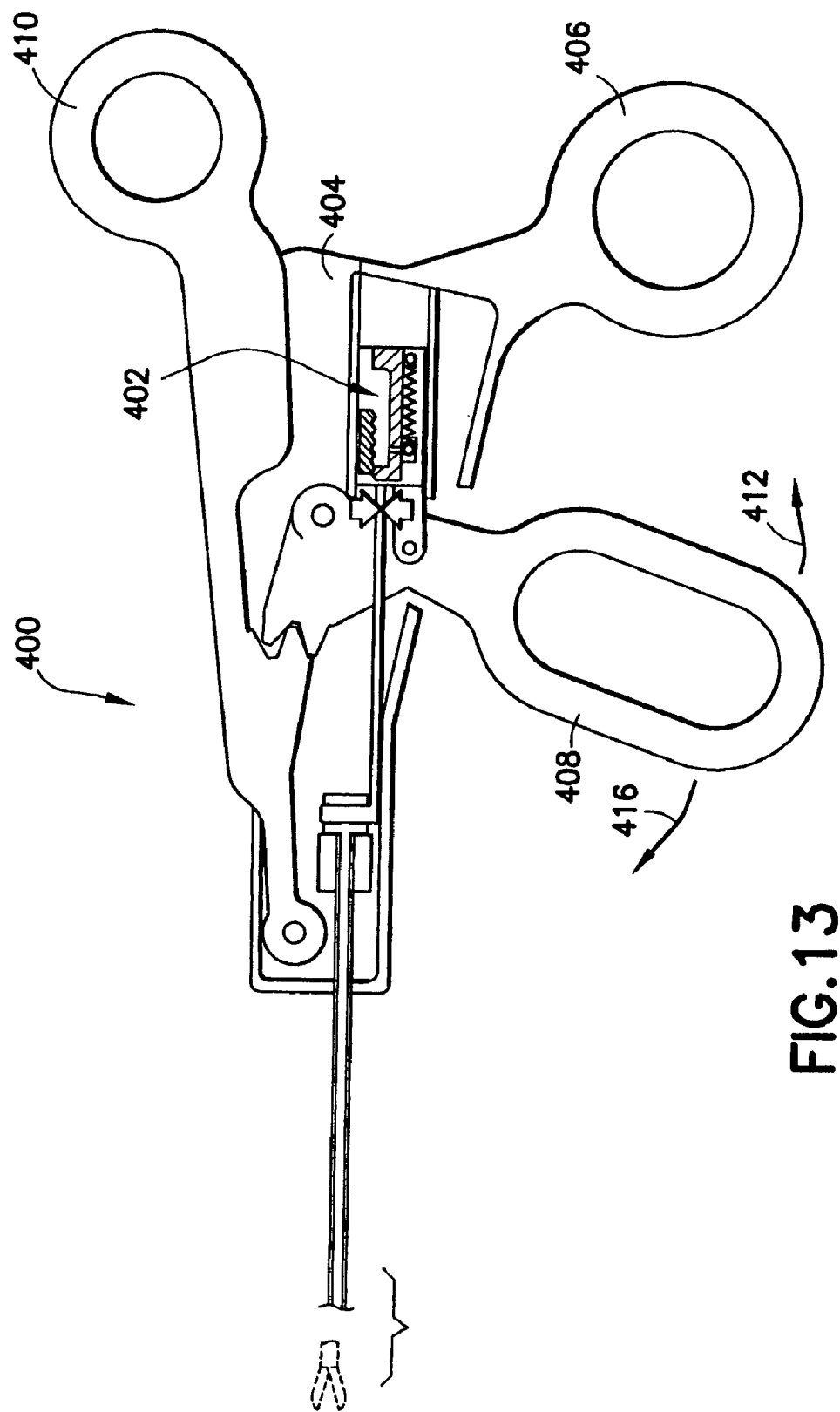
FIG. 13 is a schematic elevation view of yet another exemplary embodiment of the device.

Referring now to FIG. 13, there is shown a schematic section view of still yet another exemplary embodiment of a one hand locking and releasing apparatus 400. Referring also to FIGS. 13A, 13B, 13C and 13D there is shown a schematic section view of a locking and release mechanism 402 of the locking and releasing apparatus 400 from FIG. 13. One hand locking and releasing apparatus 400 similarly includes a handle 404, a finger loop 406 integral with the handle and first and second lever members, 408, 410 pivotally mounted movement between a first direction 412 and a second direction 416. The lever members are moveable in opposite first and second directions relative to the handle over a predetermined range of motion. A force transmitting member 420 extends away from a locking and release mechanism 402. Force transmitting member 420 through locking and release mechanism 404 operably connects the lever member 408 to the medical device.

Referring now to FIGS. 14A, 14B, 14C and 14D, locking and release mechanism 404 operably connects lever member 408 to force transmitting member 420 for operating the medical device. Locking and release mechanism 404 locks movement of the force transmitting member in two directions 436, 437 when lever member 408 is in a neutral position relative to sliding block 442 such that pin or sliding barrier 450 aligns with stanton 449 raised off of beam or flexure 448 of pawl 444 (see FIG. 14A). Sliding barrier 450 may be spring centered relative to sliding block 442 such when an operator is not exerting force to lever member 408 or otherwise, pin or sliding barrier 450 aligns with stanton 449 raised off of beam or flexure 448 of pawl 444 as shown in FIG. 14C. Locking and release mechanism 402 releases movement of the force transmitting member 420 in the either direction 436 or 437 after movement of the lever member 338 in either direction 412, 416. Lever member 408 operates the locking and release mechanism 404 releasing the movement of the force transmitting member 420 in the either direction 436, 437 substantially upon changing movement of the lever member 338 from the first 412 to the second direction 416 and vice versa. Locking mechanism 404 locks movement of the force transmitting member 420 at a locking position 438 (see FIG. 14C), located over at least part of the range of motion of lever member 408 after movement of the lever member in the first direction and subsequent slight motion in the second direction relative to block 442 such that stanton 449 aligns with pin 450 (not shown). Where pin 450 is not aligned with stanton 449, flexure 448 is free to flex allowing pawl 444 to rachet. Where pin 450 is aligned with stanton 449, flexure 448 is not free to flex locking pawl 444 relative to rack 446. Changing the direction of movement of the lever member 338 from first direction 342 where the lever member is at a locking position (i.e. pin 450 is aligned with stanton 449) causes the release mechanism 332 to release movement of force transmitting member 420 (see FIG. 14D). second direction 416 is substantially opposite of locking direction 412. Locking and release mechanism 402 has a pawl 444 and a rack 446 coupled to either force transmitting member 420 or handle 404 respectively. Pawl 444 has flexure section 448. Flexure section 448 has stanton 449 which is engaged by pin or sliding barrier 450 as a function of the relative movement between lever member 408 and pawl 444. Flexure section 448 may operate as a spring biasing pawl 444 to engage rack 446. Force transmitting member 420 is coupled to sliding block 442. Sliding block 442 is constrained to slide relative to frame 404. Rack 446, in the embodiment shown is grounded to frame 404. Pawl 444 is coupled to sliding block 442. Link 414 is pivotally coupled to lever 408. Sliding barrier 450 is coupled to link 414. Link 414 has pin or sliding barrier 450 which slides in slot 456 of sliding block 442. Pin or sliding barrier 450 in combination with slot 456 enables flexure section 448 and stanton 449 to be blocked by sliding barrier 450, preventing flexure section 448 from flexing (thus locking—see FIG. 14A) or enables flexure section 448 to not be blocked (so 444 may rachet) where sliding barrier is not aligned with stanton 449 thus releasing and allowing racheting movement (see FIG. 14B, 14C, 14D). As described, Preventing flexure section 448 from flexing through relative movement between lever member 408 and pawl 444 through link 414 determines whether pawl 444 engaging rack 446 may rachet or be locked as a function of movement of lever member 408.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A locking and releasing apparatus for operating a medical device comprising:

a handle;

a lever member coupled to the handle for grasping engagement by an operator, the lever member being moveable in opposite directions relative to the handle for effecting actuation of a force transmitting member for operating the medical device at a location distant from the handle; and a locking and release mechanism operably connecting the lever member to the force transmitting member;

wherein, the locking and release mechanism locks movement of the force transmitting member in one direction after movement of the lever member in a locking direction, and wherein, the locking and release mechanism releases movement of the force transmitting member in the one direction after opposite movement of the lever member in a releasing direction, wherein the lever member operates the locking and release mechanism for releasing the movement of the force transmitting member in the one direction substantially upon changing movement of the lever member from the locking to the releasing direction.

2. The locking and releasing apparatus for operating a medical device according to claim 1 wherein the locking and release mechanism comprises a pawl and a rack coupled to either the force transmitting member or the handle respectively, wherein the pawl engages the rack after movement of the lever member, and wherein the pawl disengages the rack after opposite movement of the lever member.

3. The locking and releasing apparatus for operating a medical device according to claim 2 wherein the pawl has a camming surface, wherein the camming surface is engaged through relative movement between the lever member and the pawl, and wherein the locking and release mechanism further comprises a spring biasing the pawl to engage the rack.

4. The locking and releasing apparatus for operating a medical device according to claim 1 wherein the releasing direction is substantially opposite of the locking direction.

5. The locking and releasing apparatus for operating a medical device according to claim 1 wherein the locking and release mechanism comprises a first wedge coupled to the force transmitting member and a second wedge slidingly coupled to the first wedge, wherein the lever member engages the first wedge or the force transmitting member in the locking direction, and wherein the lever member engages the second wedge in the releasing direction.

6. The locking and releasing apparatus for operating a medical device according to claim 5 wherein the locking and release mechanism further comprises a spring biasing wedging surfaces of the first and second wedges against each other.

7. The locking and releasing apparatus for operating a medical device according to claim 1 wherein the locking and release mechanism comprises a cleat wedge coupled to the force transmitting member, wherein the lever member engages the force transmitting member in the locking direction, and wherein the lever member releases the cleat wedge in the releasing direction.

8. A locking and releasing apparatus for operating a medical device comprising:
a handle;
a lever member mounted on the handle for grasping engagement by an operator, the lever member being moveable in opposite first and second directions relative to the handle over a predetermined range of motion for effecting actuation of a force transmitting member for operating the medical device at a location distant from the handle;
a locking mechanism operably connecting the lever member to the force transmitting member; and
a release mechanism operably connected to the lever member;
wherein, the locking mechanism locks movement of the force transmitting member at a locking position located over at least part of the range of motion of the lever member after movement of the lever member in the first direction, and wherein changing the direction of movement of the lever member from the first direction where the lever member is at the locking position causes the release mechanism to release movement of the force transmitting member.

9. The locking and releasing apparatus for operating a medical device according to claim 8 wherein the locking mechanism comprises a pawl and a rack coupled to either the force transmitting member or the handle respectively, wherein the pawl engages the rack after movement of the lever member, and wherein the pawl disengages the rack after opposite movement of the lever member.

10. The locking and releasing apparatus for operating a medical device according to claim 9 wherein the pawl has a camming surface, wherein the release mechanism engages the camming surface through relative movement between the lever member and the pawl, and wherein the locking mechanism further comprises a spring biasing the pawl to engage the rack.

11. The locking and releasing apparatus for operating a medical device according to claim 8 wherein the locking mechanism comprises a first wedge coupled to the force transmitting member and a second wedge slidingly coupled to the first wedge, wherein the lever member engages the first wedge or the force transmitting member in the first direction with the release mechanism, and wherein the lever member engages the second wedge in the second direction with the release mechanism, and wherein the locking mechanism further comprises a spring biasing wedging surfaces of the first and second wedges against each other.

12. The locking and releasing apparatus for operating a medical device according to claim 8 wherein the locking mechanism comprises a cleat wedge coupled to the force transmitting member wherein the lever member engages the force transmitting member in the first direction with the release mechanism, and wherein the lever member releases the cleat wedge in the second direction with the release mechanism.

13. A one hand locking and releasing apparatus for operating a medical device comprising:
a handle;
a finger loop mounted on the handle for receiving a finger on one hand of an operator;
first and second lever members mounted on the handle for grasping engagement by other fingers of the one hand of the operator when the finger is in the finger loop, at least one of the lever members being mounted on the handle for movement in first and second directions relative to the finger loop; and
a locking and release mechanism operably connecting at least one of the first and second lever members to a force transmitting member for operating the medical device at a location distant from the handle;
wherein, the locking and release mechanism is actuated for causing and locking movement of the force transmitting member by movement of the at least one of the lever members in the first direction, wherein the locking and release mechanism is actuated for causing and releasing movement of the force transmitting member by movement of the at least one of the lever members in the second direction, the at least one of the lever members actuating the locking and release mechanism for releasing movement substantially upon changing direction of movement of the at least one of the lever members from the first direction to the second direction, and wherein, in the course of operating the medical device, the operator can reposition his fingers of the one hand between the first and second lever members with rotation of the finger within the finger loop.

14. The one hand locking and releasing apparatus for operating a medical device according to claim 13 wherein, the locking and release mechanism locks movement of the force transmitting member after application of force by the operator to at least one of the lever members and the finger loop in the first direction, and wherein the locking and release mechanism releases movement of the force transmitting member after application of force by the operator to at least one of the lever members and the finger loop in the second direction.

15. The one hand locking and releasing apparatus for operating a medical device according to claim 13 wherein the finger loop is integral with the handle, and wherein the first lever member and the second lever member are coupled such that the first lever member and the second lever member move in a coordinated manner.

16. The one hand locking and releasing apparatus for operating a medical device according to claim 15 wherein the locking and release mechanism locks movement of the force transmitting member after movement of both of the lever members relative to the finger loop in a locking direction and, wherein the locking and release mechanism releases movement of the force transmitting member after movement of both of the lever members relative to the finger loop in a releasing direction.

17. The one hand locking and releasing apparatus for operating a medical device according to claim 15 wherein there is free play between both of the lever members and the locking and release mechanism between a locking operation and a release operation.

18. The one hand locking and releasing apparatus for operating a medical device according to claim 16 wherein the locking and release mechanism comprises a pawl and a rack coupled to either the force transmitting member or the handle respectively, wherein the pawl engages the rack after movement of the lever members in the locking direction, and wherein the pawl disengages the rack after movement of the lever members in the release direction.

19. The one hand locking and releasing apparatus for operating a medical device according to claim 16 wherein the locking and release mechanism comprises a first wedge coupled to the force transmitting member and a second wedge slidingly coupled to the first wedge, wherein at least one of the lever member engages the first wedge or the force transmitting member in the locking direction, and wherein at least one of the lever member engages the second wedge in the releasing direction.

20. The one hand locking and releasing apparatus for operating a medical device according to claim 16 wherein the locking and release mechanism comprises a cleat wedge coupled to the force transmitting member, and wherein at least one of the lever members engages the force transmitting member in the locking direction, and wherein at least one the lever members releases the cleat wedge in the releasing direction.

* * * * *